US011213281B2

(12) United States Patent
Kassab et al.

(10) Patent No.: US 11,213,281 B2
(45) Date of Patent: Jan. 4, 2022

(54) ARTERIAL SYSTEM NAVIGATION METHODS AND DEVICES AND SYSTEMS TO PERFORM THE SAME

(71) Applicant: 3DT Holdings, LLC, San Diego, CA (US)

(72) Inventors: Ghassan S. Kassab, La Jolla, CA (US); Mark Svendsen, Indianapolis, IN (US)

(73) Assignee: 3DT HOLDINGS, LLC, San Diego, CA (US)

( * ) Notice: Subject to any disclaimer, the term of this patent is extended or adjusted under 35 U.S.C. 154(b) by 958 days.

(21) Appl. No.: 14/521,148

(22) Filed: Oct. 22, 2014

(65) Prior Publication Data

US 2015/0126853 A1  May 7, 2015

Related U.S. Application Data

(60) Provisional application No. 61/894,228, filed on Oct. 22, 2013.

(51) Int. Cl.
| | |
|---|---|
| *A61B 5/053* | (2021.01) |
| *A61B 18/14* | (2006.01) |
| *A61B 17/00* | (2006.01) |
| *A61B 5/0538* | (2021.01) |
| *A61B 5/02* | (2006.01) |
| *A61B 5/06* | (2006.01) |
| *A61B 34/20* | (2016.01) |
| *A61B 5/00* | (2006.01) |
| *A61B 18/00* | (2006.01) |

(Continued)

(52) U.S. Cl.
CPC .... *A61B 17/00234* (2013.01); *A61B 5/02007* (2013.01); *A61B 5/0538* (2013.01); *A61B 5/068* (2013.01); *A61B 18/1492* (2013.01); *A61B 34/20* (2016.02); *A61B 5/02014* (2013.01); *A61B 5/6852* (2013.01); *A61B 5/6876* (2013.01); *A61B 2017/00026* (2013.01); *A61B 2018/00357* (2013.01); *A61B 2018/00404* (2013.01); *A61B 2018/00434* (2013.01); *A61B 2018/0212* (2013.01); *A61B 2034/2053* (2016.02); *A61B 2090/376* (2016.02)

(58) Field of Classification Search
CPC combination set(s) only.
See application file for complete search history.

(56) References Cited

U.S. PATENT DOCUMENTS 4,380,237 A * 4/1983 Newbower ............ A61B 5/026
600/506
4,911,174 A * 3/1990 Pederson ................ A61B 5/042
600/508

(Continued)

*Primary Examiner* — Patricia J Park
(74) *Attorney, Agent, or Firm* — William F. Ward

(57) ABSTRACT

Arterial system navigation methods and devices and systems to perform the same. In an exemplary embodiment of a method of the present disclosure, the method comprises the steps of inserting at least part of an impedance device into an artery of a patient, the artery selected from the group consisting of a femoral artery and a radial artery, obtaining at least one conductance measurement while navigating a distal end of the impedance device through an arterial vasculature of the patient until the distal end is at or near a left ventricle, and performing at least one medical procedure at a location within the arterial vasculature.

20 Claims, 4 Drawing Sheets

(51) Int. Cl.
*A61B 18/02* (2006.01)
*A61B 90/00* (2016.01)

(56) References Cited

U.S. PATENT DOCUMENTS

| | | | | |
|---|---|---|---|---|
| 5,078,678 A * | 1/1992 | Katims | ................... | A61B 5/042 |
| | | | | 600/547 |
| 8,388,546 B2 * | 3/2013 | Rothenberg | ......... | A61B 5/0422 |
| | | | | 600/508 |
| 8,597,193 B2 * | 12/2013 | Grunwald | ............ | A61B 5/0456 |
| | | | | 600/468 |
| 2005/0148832 A1 * | 7/2005 | Reghabi | ................. | A61B 5/412 |
| | | | | 600/309 |
| 2005/0256521 A1 * | 11/2005 | Kozel | ................... | A61B 5/0422 |
| | | | | 606/41 |
| 2008/0190438 A1 * | 8/2008 | Harlev | ................. | A61B 5/0536 |
| | | | | 128/898 |
| 2008/0194996 A1 * | 8/2008 | Kassab | ................... | A61B 5/053 |
| | | | | 600/593 |
| 2009/0182287 A1 * | 7/2009 | Kassab | ............. | A61B 5/02007 |
| | | | | 604/264 |
| 2009/0259124 A1 * | 10/2009 | Rothenberg | ......... | A61B 5/0422 |
| | | | | 600/424 |
| 2010/0010503 A1 * | 1/2010 | Kassab | ................ | A61B 5/0215 |
| | | | | 606/129 |
| 2010/0030055 A1 * | 2/2010 | Kassab | ................... | A61B 5/053 |
| | | | | 600/374 |
| 2012/0029496 A1 * | 2/2012 | Smith | ................... | A61B 18/02 |
| | | | | 606/21 |
| 2012/0108950 A1 * | 5/2012 | He | ......................... | A61B 5/068 |
| | | | | 600/411 |
| 2013/0178910 A1 * | 7/2013 | Azamian | ................ | A61B 18/24 |
| | | | | 607/33 |

\* cited by examiner

ARTERIAL SYSTEM NAVIGATION METHODS AND DEVICES AND SYSTEMS TO PERFORM THE SAME

PRIORITY

The present application is related to, and claims the priority benefit of, U.S. Provisional Patent Application Ser. No. 61/894,228, filed Oct. 22, 2013, the contents of which are hereby incorporated by reference in their entirety into the present disclosure.

BACKGROUND

Coronary interventional procedures are being performed more common than ever, with over two million coronary diagnostic procedures performed each year. Due to narrowing of arteries from vascular disease, narrow wires are frequently inserted into a peripheral arterial vessel, such as the femoral artery, the radial artery, etc. with the tip of the wire ultimately delivered to the left ventricle of the heart. This is currently performed under x-ray, and because the procedure can take several minutes to ultimately deliver the tip of the wire, there is an x-ray exposure risk to the patient and a significant x-ray exposure risk to the interventionalist/physician, who may perform many of these procedures in a cath lab each day over a period of several years, if not decades.

After delivery of a wire, for example, so that the tip is located at the ostia of two major coronary arties, a catheter can be advanced over the wire so to deliver a contrast agent and to obtain images to identify the contrast.

In view of the same, methods of delivering devices (wires or catheters) through a patient's arterial system, so as to significantly reduce the risk of x-ray exposure and to eliminate the need for contrast injection, unless desired to obtain vascular images, for example, would be well appreciated in the marketplace.

BRIEF SUMMARY

The present disclosure includes disclosure of various methods of navigating a portion of a patient's arterial system using exemplary devices of the present disclosure. In an exemplary embodiment of a method of the present disclosure, the method includes the step of inserting a distal end of a device into a patient's artery. In another embodiment, the method further includes the step of advancing the distal end of the device through at least part of the patient's arterial system. In an additional embodiment, the method is performed using a device comprising an elongated body having at least one detector thereon, the detector configured to obtain conductance data within the arterial system using impedance.

In an exemplary embodiment of a method of the present disclosure, the method is performed for the purpose of navigating through the portion of the patient's arterial system. In an additional embodiment, the method is performed to obtain conductance data at various locations within the patient's arterial system, said conductance data including at least one characteristic indicative of a location within the arterial system. In an additional embodiment, the method comprises performance of a medical procedure step. In another embodiment, the medical procedure step includes performing a biopsy procedure.

In an exemplary embodiment of a method of the present disclosure, the medical procedure step includes performing a coronary intervention procedure, including, but not limited to, placing a stent, placing a valve, replacing a valve, performing a transcatheter aortic valve implantation (TAVI) procedure, closing an opening within the vasculature, cauterizing (e.g., ablation) part of the vasculature or heart, and treating an aneurysm. In another embodiment, the medical procedure step includes performing a sensor placement procedure. In yet another embodiment, the medical procedure step includes delivering a medicament. In an additional embodiment, the medical procedure step includes delivering a catheter over the device.

In an exemplary embodiment of a method of the present disclosure, the step of advancing is performed to detect and/or diagnose a patient condition, such as, for example, a calcified aortic stenosis (CAS), arterial narrowing, and an aneurysm. In another embodiment, at least one method is performed to deliver a device of the present disclosure, configured as a wire or a catheter, so that the distal end of the device is positioned at a desired location within a patient. Various methods of the present disclosure are performed using impedance, so to obtain conductance data in connection with navigation, as an alternative to delivering the device using x-ray.

In at least one method of the present disclosure, the method further comprises delivering a contrast agent through the device, or through a catheter advanced over the device, and obtaining one or more images of the patient's vasculature in connection with the contrast agent. In another embodiment, at least one method is performed to deliver ablation energy to sites of the vasculature for therapy, such as renal ablation for the treatment of hypertension.

In an exemplary embodiment of a system of the present disclosure, the system comprise an exemplary device of the present disclosure and at least one other element, which can be one or more of a console, a second device, a lead, a medicament, and a catheter, as referenced, described, and/or shown herein.

In an exemplary embodiment of a method of the present disclosure, the method comprises the steps of inserting at least part of an impedance device into an artery of a patient, the artery selected from the group consisting of a femoral artery and a radial artery, obtaining at least one conductance measurement while navigating a distal end of the impedance device through an arterial vasculature of the patient until the distal end is at or near a left ventricle, and performing at least one medical procedure at a location within the arterial vasculature. In another embodiment, the at least one conductance measurement includes at least one characteristic indicative of a location with the arterial vasculature. In yet another embodiment, the step of obtaining the at least one conductance measurement comprises obtaining a plurality of conductance measurements within the arterial vasculature. In an additional embodiment, the plurality of conductance measurements each includes at least one characteristic indicative of a location with the arterial vasculature.

In an exemplary embodiment of a method of the present disclosure, the at least one medical procedure is selected from the group consisting of a biopsy procedure, a coronary intervention procedure, and a sensor placement procedure. In an additional embodiment, the at least one medical procedure is selected from the group consisting of a transcatheter aortic valve implantation (TAVI) procedure, a valve placement procedure, a valve replacement procedure, and a stent placement procedure. In yet an additional embodiment, the at least one medical procedure is selected from the group consisting of closing an opening within the arterial vasculature and cauterizing part of the arterial vasculature or heart. In another embodiment, the at least one medical procedure comprises treating an aneurysm. In yet another embodiment, the at least one medical procedure comprises delivering a medicament.

In an exemplary embodiment of a method of the present disclosure, a patient condition is detected and/or diagnosed while navigating the distal end of the impedance device through the arterial vasculature. In another embodiment, the patient condition is selected from the group consisting of a calcified aortic stenosis (CAS), arterial narrowing, and an aneurysm. In yet another embodiment, navigation of the distal end of the impedance device is performed to position the distal end at a desired location within the arterial vasculature. In an additional embodiment, the method is performed without requiring x-ray.

In an exemplary embodiment of a method of the present disclosure, the method further comprises the steps of delivering a contrast agent through the impedance device or through a catheter advanced over the impedance device, and obtaining one or more images of the arterial vasculature in connection with the contrast agent. In an additional embodiment, the at least one medical procedure involves delivering ablation energy to one or more locations within the arterial vasculature to treat hypertension. In yet an additional embodiment, the artery is the femoral artery, and wherein navigation of the distal end of the impedance device is performed by navigating the distal end from the femoral artery to the iliac artery, past the renal artery bifurcation to the abdominal aorta, to the thoracic aorta, to the aortic arch, and to the left ventricle. In another embodiment, the impedance device comprises an elongated body having at least one detector thereon, the detector configured to obtain the at least one conductance measurement within the arterial vasculature using impedance.

In an exemplary embodiment of a method of the present disclosure, the method comprises the steps of inserting at least part of an impedance device into an artery of a patient, the artery selected from the group consisting of a femoral artery and a radial artery, obtaining a plurality of conductance measurements while navigating a distal end of the impedance device from the artery, through an arterial vasculature of the patient, and to a location at or near a left ventricle, each of the plurality of conductance measurements including at least one characteristic indicative of a location within the arterial vasculature, and performing at least one medical procedure at a targeted location within the arterial vasculature, the targeted location identified from at least one of the plurality of conductance measurements.

In an exemplary embodiment of a method of the present disclosure, the method comprises the steps of inserting at least part of an impedance device into an artery of a patient, the artery selected from the group consisting of a femoral artery and a radial artery, obtaining a first conductance measurement while a distal end of the impedance device is positioned within an arterial vasculature of the patient at a first location, obtaining a second conductance measurement while the distal end of the impedance device is positioned within the arterial vasculature at a second location, moving the distal end of the impedance device to a third location within the arterial vasculature based upon the first conductance measurement and the second conductance measurement, moving the distal end of the impedance device to a fourth location within the arterial vasculature based upon at least the third conductance measurement, ultimately moving the distal end so that it is positioned at or near a left ventricle, said movement performed based upon one or more additional conductance measurements obtained within the arterial vasculature, and performing at least one medical procedure at a location within the arterial vasculature. In another embodiment, the first conductance measurement, the second conductance measurement, the third conductance measurement, the fourth conductance measurement, and the one or more additional conductance measurements are each obtained using a detector of the impedance device.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

DETAILED DESCRIPTION

Figure 1A:
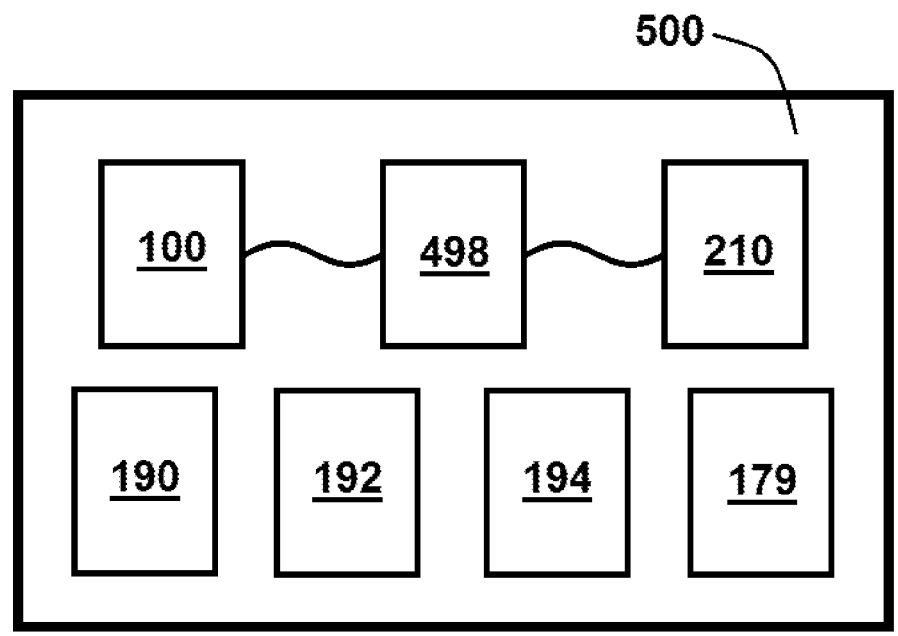
FIG. 1A shows a block component diagram of a system, according to an exemplary embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary system of the present disclosure is shown in FIG. 1A in block diagram component form. As shown therein, an exemplary system 500 of the present disclosure comprises an exemplary device 100 (configured as a wire or catheter, as referenced in detail herein) of the present disclosure and at least one additional component/element, such as a console 210. Console 210, in various embodiments, may comprise a general data acquisition and processing system, such as a computer or a device having computing componentry, a screen, an optional keyboard, etc. An exemplary device 100 of the present disclosure, along with at least an exemplary console 210 of the present disclosure, comprises an exemplary system 500 of the present disclosure, as shown in FIG. 1A. Device 100 may connect directly to console 210, or indirectly to console 210 via connector 498 positioned therebetween, as shown in FIG. 1. Connector 498, in various embodiments, could comprise a handle for device 100 and/or another coupler device used to connect device 100 to console 210.

Figure 1B:
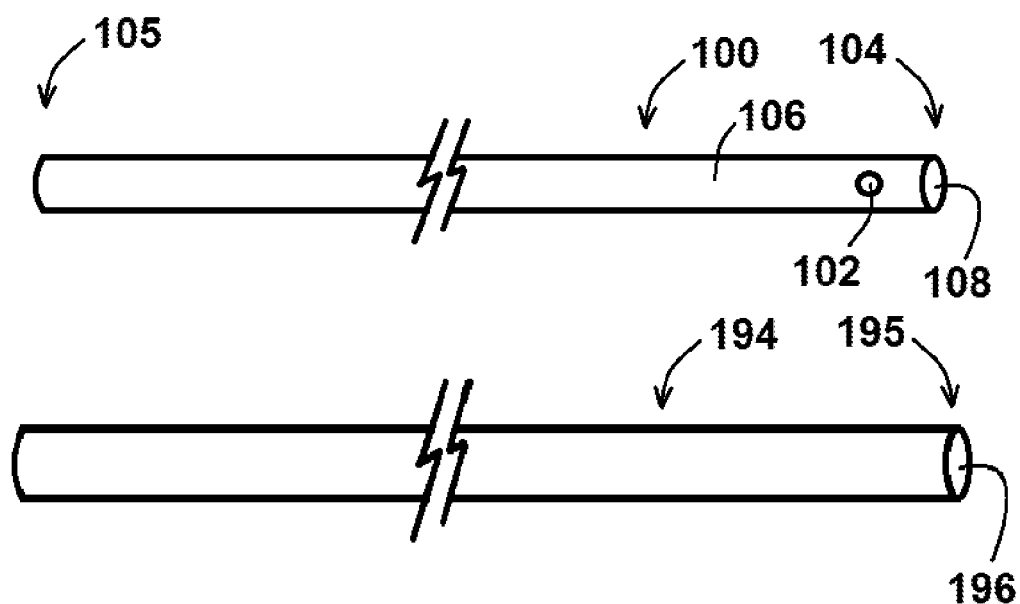
FIG. 1B shows a device and a catheter, according to an exemplary embodiment of the present disclosure.

An exemplary device of the present disclosure may be as shown in FIG. 1B and described herein. For example, and as shown in FIG. 1B, an exemplary device 100 of the present disclosure comprises an elongated body 106, having a length sufficient so that part of device 100 can be advanced from a location away from the patient's heart, such as the patient's femoral artery, radial artery, or any number of other arteries (including other peripheral arterial vessels), to a location at or near the patient's heart, while permitting a portion of device 100 to remain outside of the patient's body (so to facilitate navigation, for example). Device 100, as shown in FIG. 1B, may further comprise at least one detector 102 positioned at or near a distal end 104 of elongated body 106, and may further comprise at least one lumen 108 defined through elongated body 106, extending from distal end 104 to proximal end 105 of the elongated body. Detectors 102, as referenced herein, may comprise one or more impedance electrodes capable of generating an electric field within a patient's body, such as by way of one, two or more electrodes on elongated body 106 to generate the field and/or at least one electrode on elongated body 106 and at least another electrode outside of the patient's body that are used to generate the field.

Figure 2:
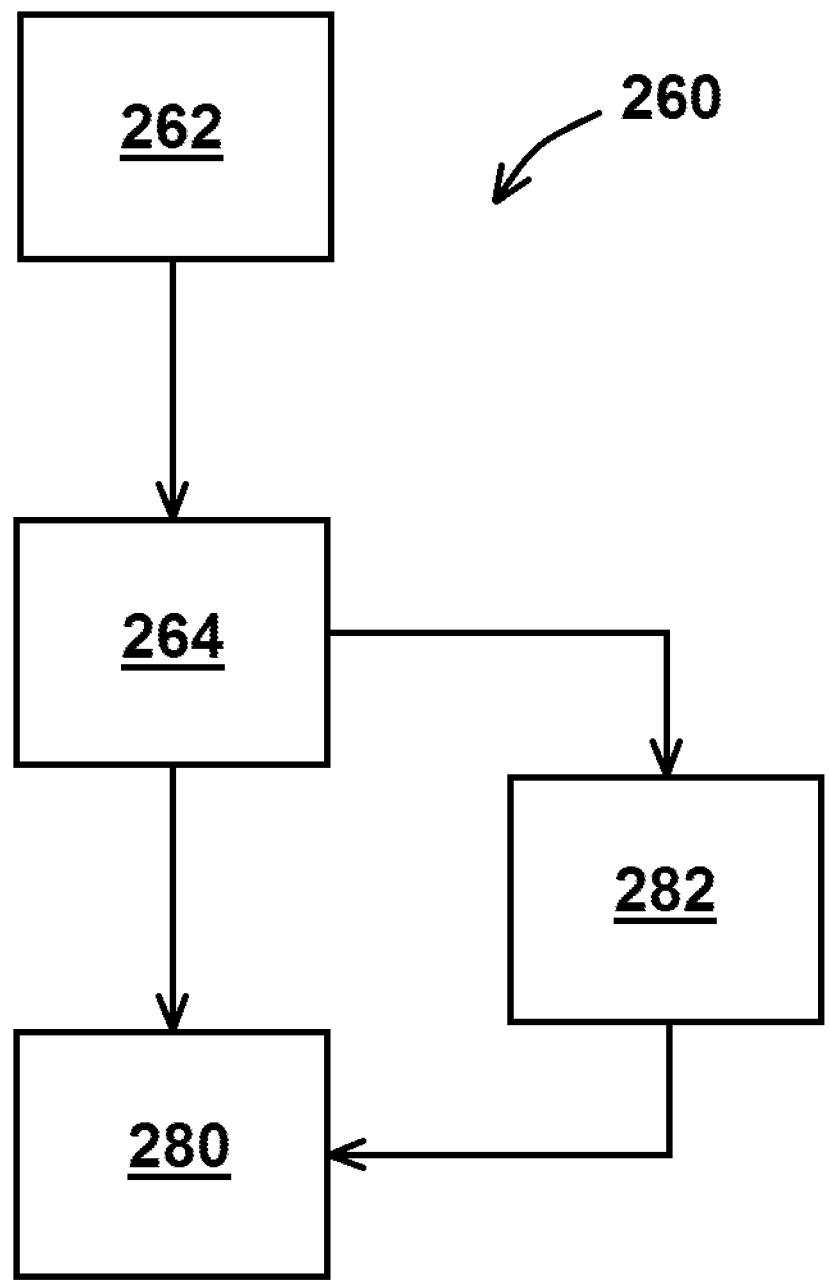
FIGS. 2 and 3 show steps of methods in block step form, according to an exemplary embodiment of the present disclosure.
Figure 3:
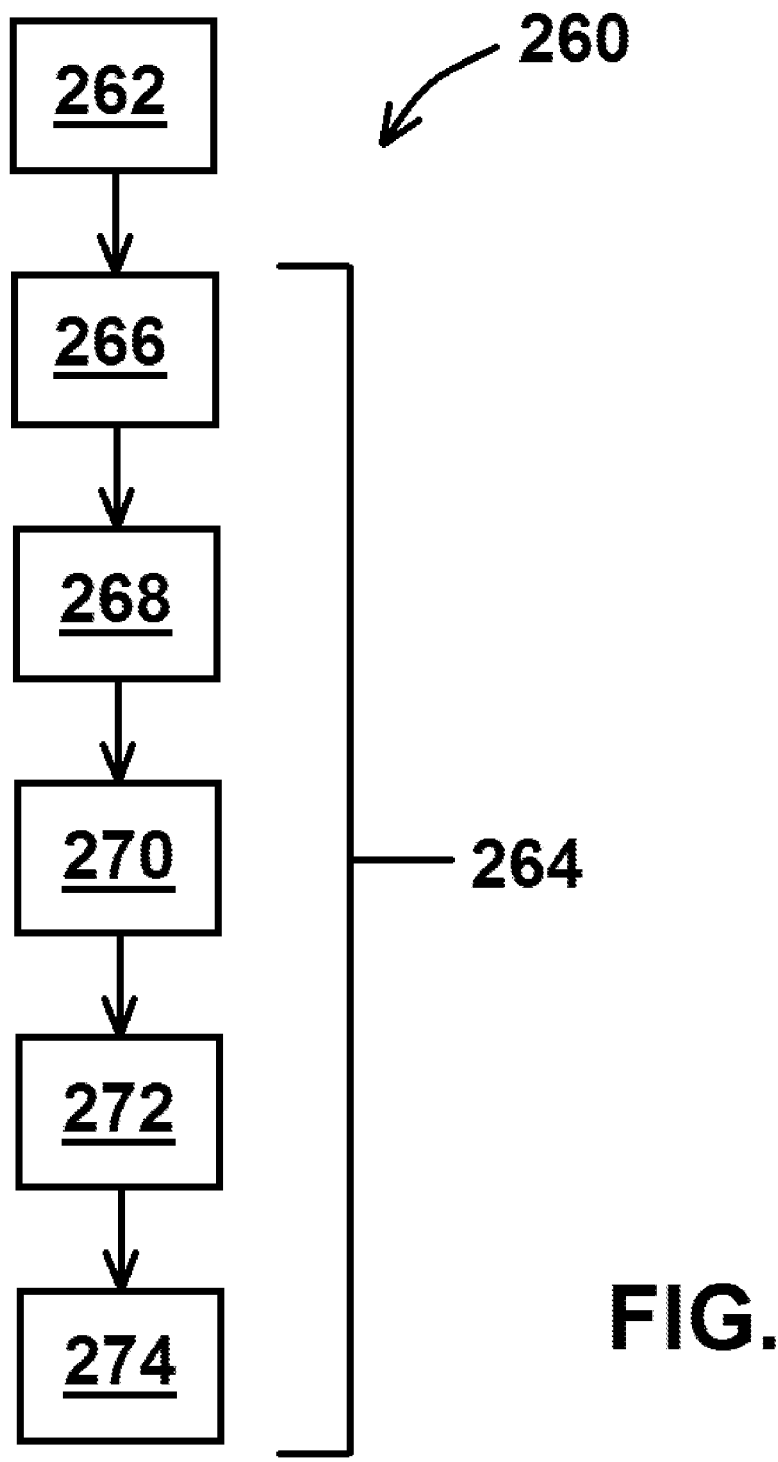

In at least one exemplary method 260 of the present disclosure, as shown in block step format in FIG. 2, an exemplary device 100 of the present disclosure is inserted into a patient's femoral artery (an exemplary device insertion step 262), and advanced therethrough so that the tip (distal end 104 of device 100) ultimately reaches the patient's left ventricle (an exemplary advancement step 264). In such an advancement, for example, distal end 104 of device 100 would advance from the femoral artery to the iliac artery, the abdominal aorta, the thoracic aorta, and ultimately to the left ventricle so that the tip (distal end 104 of device 100) is present therein. As such, an exemplary advancement step 264 may comprise several substeps, such as the substep of moving distal end 104 through the femoral artery to the iliac artery (substep 266), moving from the iliac artery through the abdominal aorta while passing by the renal artery bifurcation (substep 268), moving past the renal artery bifurcation in the abdominal aorta to the thoracic aorta (substep 270), moving from the thoracic aorta to aortic arch (substep 272), and moving from the aortic arch to a location at or near the left ventricle (substep 274), as shown in FIG. 3.

Figure 4:
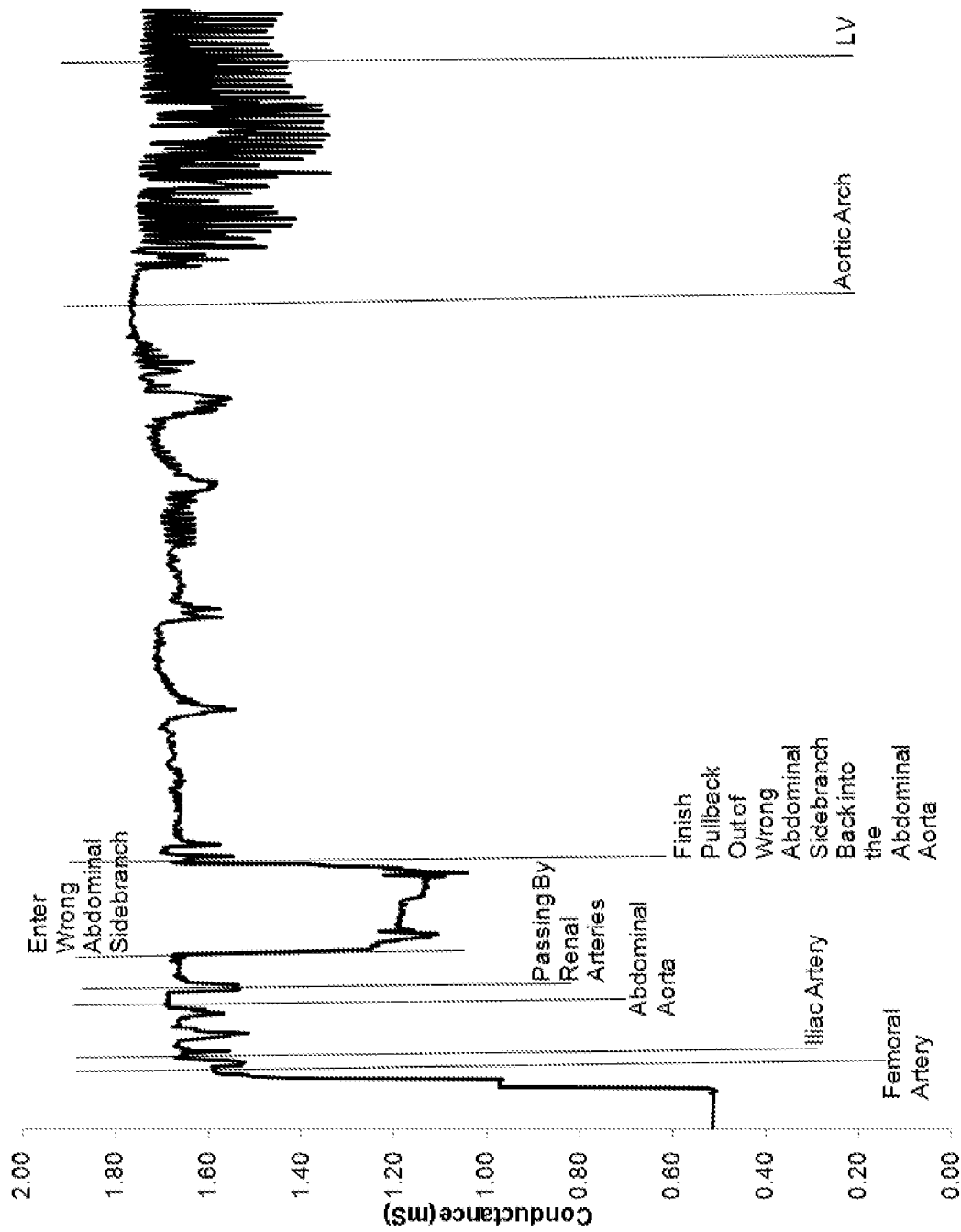
FIG. 4 shows a conductance curve/chart obtained by using a device, according to an exemplary embodiment of the present disclosure; and An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

In such an advancement, for example, distal end 104 of device 100 generally moves from the femoral artery, to the iliac artery, to the abdominal aorta, to the thoracic aorta, to the aortic arch, and into the left ventricle, as shown in FIG. 4. As shown in the conductance curve in FIG. 4, conductance increases sharply as distal end 104 of device 100 moves from the femoral artery to the iliac artery, with waves of conductance generally leveling off at or near the iliac artery and at the abdominal aorta. Changes in conductance are relatively minor, with small changes and initial pulsatility due to blood flow identified as distal end 104 of device 100 approaches the thoracic aorta. When entering a side branch, conductance decreases sharply, but returns back to normal baseline levels once device 100 is retracted back into the desired path in the abdominal aorta. Advancement to the heart then continues in a normal manner as conductance is relatively stable with relatively small changes associated with passing by side branches, etc. Conductance approaches its largest value with little pulsatility at the level of the aortic arch. Pulsatility increases greatly as distal end 104 of device approaches the left ventricle, serving as a visual indicator to the user of device 100 that distal end 104 is at or near the left ventricle. The conductance curve shown in FIG. 4 was obtained in real time (y-axis can be considered as "time" if advancement is constant, but as shown in FIG. 4, y-axis relates to location within the arterial vasculature during advancement, which occurs over time), and is a visual snapshot of a result that would otherwise be made available visually to the user in real time by way of console 210, for example, operably connected to device 100.

In addition, advancement step 264, as referenced herein, may be performed so to identify a specific location within a patient's arterial system. For example, and as described above, exemplary conductance curves/charts can be identified by way of performing various methods 260 of the present disclosure, noting that said curves/charts have characteristics relating to specific locations within the vasculature as described above and as shown in FIG. 4. In view of the same, and for example, a user of device 100, while performing method 260 of the present disclosure, would know that a distal end 104 of device 100 (or the portion of device 100 having at least one detector 102 therein/thereon, as detector 102 is used to obtain the conductance data referenced herein), is in the abdominal aorta between the renal artery and the start of the thoracic artery by identifying initial pulsatility due to blood flow, for example. In view of the foregoing, multiple conductance measurements can be obtained during navigation, and prior conductance measurements can be considered when performing additional navigation. As noted above, for example, entry of a side branch can cause conductance to drop, which tells the navigator to pull back and re-navigate forward until the conductance measurements are as expected (relatively the same or larger, for example, as indicated in FIG. 4). Accordingly, a user may obtain a first and a second conductance measurement, or a plurality of initial conductance measurements such as shown in FIG. 4, and will continue to navigate in view of the same, whereby navigation continues based upon at least one or more of the earlier-obtained conductance measurements.

Various devices 100 of the present disclosure may be generally referred to as ultra-sound friendly devices, which can be used instead of angiography while reducing or eliminating x-ray exposure.

In at least one embodiment of a method 260 of the present disclosure, x-ray or other imaging may be used for final confirmation of tip (distal end 104, relating to the position of detector(s) 102 of device 100) location if desired (an exemplary tip confirmation step 282 of the present disclosure), such as so that the interventionalist/physician can obtain a second confirmation of tip location above and beyond the confirmation obtained by performing an exemplary method 260 of the present disclosure using impedance (to obtain conductance data). In such a method, x-ray or other imaging usage is not eliminated, but it is significantly reduced.

Methods 260 of the present disclosure can be performed to navigate a device 100 through a portion of an arterial vasculature, and may also be performed to determine the location of the tip (distal end 104, relating to the position of detector(s) 102 of device 100) or another portion of device 100 in connection with said navigation. Location, as described herein, is based upon data obtained in connection with one or more sensor elements (detector(s) 102) of device 100, with said detector(s) 102 added to device 100 as a component and/or forming/being part of device 100, such as a non-insulated portion of device 100. Should such a sensor element (detector 102) be positioned/located at or near a distal end 104 of device 100, data obtained from said detector 102 would be indicative of tip location. Should sensor element (detector 102) be positioned/located at a different location of device 100, data obtained from that sensor element (detector 102) would be indicative of that different location.

As such, and in view of the foregoing, various methods 260 of the present disclosure can be performed for device 100 navigation and for general tip location, as desired. Abnormalities of the patient's arterial vasculature can be diagnosed along the way (during navigation), such as, for example, atherosclerosis, calcification, vessel dilation due to aneurysm, vascular dissections (splits that impinge on the vessel lumen), and others, by way of obtaining impedance measurements within said arterial vasculature. Deviations from expected conductance curves/charts, such as unexpected increases or decreases in conductance, less pulsatility than expected, etc., at various locations may be useful indicators of one or more of the aforementioned abnormalities. For example, a normal human aorta is generally cylindrical, and a non-cylindrical aorta would indicate some sort of abnormality, as would be indicated by a deviation from an expected conductance curve/chart at that particular location within the patient's arterial system.

Navigation, such as during advancement step 264, can be performed using impedance as referenced herein (resulting in obtaining conductance data), which can be an alternative to traditional navigation performed under x-ray, so to reduce the risk of x-ray exposure, especially to the person navigating device 100.

Calcified aortic stenosis (CAS) is a significant problem for the elderly. Patients with this condition experiencing chest pain or suspecting that they have some sort of coronary artery disease may actually have CAS. By performing an exemplary method 260 of the present disclosure, arterial narrowing would be identified during at least a portion of the arterial navigation for patients having coronary artery disease, but may not be identified in patients having certain symptoms tied to CAS. As such, at least one method 260 of the present disclosure can be performed to detect and/or diagnose CAS by way of navigating a device 100 through the patient's arterial vasculature and identifying no or relatively little arterial narrowing due to plaque and/or other arterial vessel buildup, which would occur during or in connection with an exemplary advancement step 264 of the present disclosure. A patient with CAS would demonstrate a narrowed aortic valve, which is currently done using CT (equivalent exposure to approximately 400 x-rays).

As referenced above, an exemplary method 260 of the present disclosure can be performed to detect CAS. In an additional embodiment, method 260 is performed to diagnose an aneurysm. In the case of an aneurysm, the luminal organ can expand for a time period before diagnosis, which may be tied to the patient experiencing some pressure and/or pain. Said patient would typically get an MRI or CT in attempt to learn what may be going on, but many aneurysms generally go undiagnosed. In view of the same, various methods 260 of the present disclosure can be performed to detect the presence of an aneurysm within a mammalian patient by identifying changes in conductance, as identified in a conductance curve/chart, that would indicate a larger sized vessel at a particular location than expected (such as a vessel with an aneurysm).

A patient can have a normal coronary artery, but a narrow aorta. In such a situation, the heart tries harder to pump blood through a narrowed aorta & calcified valve. Identification of the aortic valve, for example, can be performed using various methods 260 of the present disclosure. As noted herein, x-ray is generally used to identify the location of an aortic valve, but performing various methods 260 of the present disclosure can yield accurate valve location without the prolonged use of x-ray by way of one or more identified characteristics in a conductance curve/chart obtained using device 100 during the performance of method 260.

Additional exemplary methods of the present disclosure, as shown in FIG. 2, may involve steps relating to the performance of a medical procedure aside from advancement of a device 100 into a patient's arterial system as generally referenced herein. For example, and as shown in FIG. 2, exemplary methods 260 of the present disclosure may include the step of performing at least one medical procedure (medical procedure step 280), which may include, for example, one or more of the following:

(a) performing a biopsy procedure—such an exemplary medical procedure step 280 may involve advancing a second device 190 within at least one lumen 108 defined within elongated body 106 of device 100, wherein said second device 190 is configured as a biopsy device capable of removing tissue from inside of a patient.

(b) performing a coronary invention procedure—such an exemplary medical procedure step 280 may involve advancing a second device 190 within at least one lumen 108 defined within elongated body 106 of device 100, wherein said second device 190 is configured as a stent, a valve, a stent valve, a cauterizing device, a stitching device, and/or other devices known in the art configured to fit within a lumen 108 of a device 100 (or configured for advancement alongside device 100) and configured to fit within a patient's arterial vasculature and configured to perform at least one coronary intervention procedure. Said procedure may involve placing a stent, placing a valve, replacing a valve, performing a traditional transcatheter aortic valve implantation (TAVI) procedure, closing an opening within the vasculature, cauterizing part of the vasculature or heart, treating an aneurysm, etc.

(c) performing a sensor placement procedure—such an exemplary medical procedure step 280 may involve advancing a second device 190 within at least one lumen 108 defined within elongated body 106 of device 100, wherein said second device 190 is configured as a device capable of placing a lead 192 (shown in FIG. 1A as part of an exemplary system 500, but also considered as a separate device) or another sensor within a patient.

(d) delivering a medicament—such an exemplary medical procedure step 280 may involve delivering an agent 179 (such as a drug) within at least one lumen 108 defined within elongated body 106 of device 100, or through a catheter advanced over said device 100 (as described in further detail herein) so that the drug exits lumen 108 at distal end 104 of device 100 or a lumen 108 of the catheter and into a location within the patient.

(e) advancing a catheter over said device 100, as described in further detail below.

(f) delivering a contrast agent—such an exemplary medical procedure step 280 may involve delivering an agent 179 (such as a contrast agent) within at least one lumen 108 defined within elongated body 106 of device 100, or through a catheter advanced over said device 100 (as described in further detail herein) so that the contrast agent exits lumen 108 at distal end 104 of device 100 or a lumen of the catheter and into a location within the patient, and wherein one or more images of the patient's vasculature can be obtained in connection with said contrast agent.

(g) delivering ablation energy to sites of the vasculature for therapy, such as renal ablation for the treatment of hypertension. In this case, the navigation is made to the renal artery where a device 100 is delivered to the lumen of the vessel that delivers a radio frequency (RF), cryo- or other forms of energy to denervate the vessel.

During the performance of various methods 260 of the present disclosure, advancement of a portion of a device 100 should ideally not be into the coronary artery. For example, a tip (distal end 104) of device 100 can be advanced through a portion of the patient's arterial system to a desired location, and a catheter 194 (shown in FIG. 1A as part of an exemplary system 500, but also considered as a separate device as shown in FIG. 1B) can be advanced over device 100 so that a distal portion (such as distal end 195) of catheter 194 is at or near the tip 104 of device 100. Device 100 may be a first wire, such as a wire having an 0.014" or 0.035" outer diameter (or another diameter), and may also be exchanged for a second wire by, for example, advancing a first larger wire (such as an 0.035" wire) into the arterial system, advancing a catheter over said wire, removing said wire, and inserting a second smaller wire (such as an 0.014" wire) into a lumen 196 of the catheter 194. Device 100 may also be considered as a catheter, as shown in FIG. 1B, having a lumen 108 therethrough. Device 100 can then be removed, leaving catheter 194 in place for a desired period of time, whereby catheter 194 can serve as the device used to provide access to the heart and/or to a location distal to distal end 195 of catheter 194 within the patient.

In addition, and in general, interventional cardiologists do not perform diagnostic procedures, as they work with others who ultimately place a catheter 194 over a wire (which can now be an exemplary device 100 of the present disclosure) after the tip 104 of device 100 has been delivered to the ostia for injection of contrast.

As generally referenced herein, conductance curves/charts have specific characteristics that would generally become "expected" as a user performs several methods 260 of the present disclosure, with deviations from the norm being indicative of a potential condition as referenced herein. In addition, deviations from the norm could also be indicative of advancement to an unintended vessel, such as unexpected conductance, lack of or less pulsatility, etc., and in such a situation the user can partially retract device 100 and attempt to advance once again.

Other method 260 embodiments or uses of device 100 other than as described above are also contemplated. For example, advancement step 264 may be performed to advance a distal end 104 of device 100 from one femoral artery to another, or from one artery to another artery within the patient other than those specifically referenced above. For example, it may be desired to perform device insertion step 262 at one artery and advance a distal end 104 of device 100 to the heart, the carotid artery, or to another location within the arterial vasculature. By way of a specific example, insertion step 262 can be performed to insert device 100 into the radial artery, and advancement step 264 can be performed to advance distal end 104 of device 100 into the heart, for example.

While various embodiments of arterial system navigation devices and systems and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method, comprising the steps of:
inserting at least part of an impedance device into a femoral artery of a patient, the at least part of the impedance device comprising a solitary electrode;
generating an electric field from the solitary electrode on the at least part of the impedance device within a patient's body;
obtaining at least one conductance measurement while navigating a distal end of the impedance device from the artery and through an arterial vasculature of the patient without utilizing x-ray or other imaging devices;
wherein the at least one conductance measurement includes at least one characteristic indicative of a location within the arterial vasculature; and
wherein the step of obtaining at least one conductance measurement while navigating the distal end of the impedance device further comprises steps of:
obtaining a first conductance measurement in the femoral artery from the solitary electrode;
advancing the distal end of the impedance device from the femoral artery to an iliac artery and obtaining a second conductance measurement from the solitary electrode when the distal end of the impedance device is in the iliac artery, the second conductance measurement comprising an increase from the first conductance measurement; and
advancing the distal end of the impedance device to an abdominal aorta of the patient based on the second conductance measurement.

2. The method of claim 1, wherein the step of obtaining the at least one conductance measurement comprises obtaining a plurality of conductance measurements within the arterial vasculature, wherein at least one of the plurality of conductance measurements are obtained while navigating the distal end of the impedance device through the arterial vasculature of the patient.

3. The method of claim 2, wherein the plurality of conductance measurements each include at least one characteristic indicative of a location with the arterial vasculature.

4. The method of claim 1, further comprising the step of performing at least one medical procedure, wherein the at least one medical procedure is selected from the group consisting of a biopsy procedure, a coronary intervention procedure, and a sensor placement procedure.

5. The method of claim 1, further comprising the step of performing at least one medical procedure, wherein the at least one medical procedure is selected from the group consisting of a transcatheter aortic valve implantation (TAVI) procedure, a valve placement procedure, a valve replacement procedure, and a stent placement procedure.

6. The method of claim 1, further comprising the step of performing at least one medical procedure, wherein the at least one medical procedure is selected from the group consisting of closing an opening within the arterial vasculature and cauterizing part of the arterial vasculature or heart.

7. The method of claim 1, further comprising the step of performing at least one medical procedure, wherein the at least one medical procedure comprises treating an aneurysm.

8. The method of claim 1, further comprising the step of performing at least one medical procedure, wherein the at least one medical procedure comprises delivering a medicament.

9. The method of claim 1, wherein a patient condition is detected and/or diagnosed while navigating the distal end of the impedance device through the arterial vasculature.

10. The method of claim 9, wherein the patient condition is selected from the group consisting of a calcified aortic stenosis (CAS), arterial narrowing, and an aneurysm.

11. The method of claim 1, wherein navigation of the distal end of the impedance device is performed to position the distal end at a desired location within the arterial vasculature.

12. The method of claim 1, further comprising the step of using x-ray or other imaging for final confirmation of the distal end location.

13. The method of claim 1, further comprising the steps of:
delivering a contrast agent through the impedance device or through a catheter advanced over the impedance device; and
obtaining one or more images of the arterial vasculature in connection with the contrast agent.

14. The method of claim 1, further comprising the step of performing at least one medical procedure, wherein the at least one medical procedure involves delivering ablation energy to one or more locations within the arterial vasculature to treat hypertension.

15. The method of claim 1, wherein navigation of the distal end of the impedance device is performed by navigating the distal end from the femoral artery to the iliac artery, past a renal artery bifurcation to the abdominal aorta, to a thoracic aorta, to an aortic arch, and to a left ventricle.

16. The method of claim 1, wherein the impedance device comprises an elongated body having at least one detector thereon, the detector configured to obtain the at least one conductance measurement within the arterial vasculature using impedance.

17. A method, comprising the steps of:
inserting at least part of an impedance device into a femoral artery of a patient, the at least part of the impedance device comprising a solitary electrode;
generating an electric field using both the solitary electrode on the at least part of the impedance device within a patient's body and at least another electrode outside of the patient's body;
obtaining a plurality of conductance measurements while navigating a distal end of the impedance device from the artery and through an arterial vasculature of the patient without utilizing x-ray or other imaging devices, each of the plurality of conductance measurements including at least one characteristic indicative of a location within the arterial vasculature;
wherein the plurality of conductance measurements comprises a first conductance measurement and a second conductance measurement;
wherein the step of obtaining the plurality of conductance measurements while navigating the distal end of the impedance device further comprises steps of:
obtaining the first conductance measurement in the femoral artery from the solitary electrode;
advancing the distal end of the impedance device from the femoral artery to an iliac artery and obtaining the second conductance measurement from the solitary electrode when the distal end of the impedance device is in the iliac artery, the second conductance measurement comprising an increase from the first conductance measurement; and
advancing the distal end of the impedance device to an abdominal aorta of the patient based on the second conductance measurement;
comparing the plurality of conductance measurements to a plurality of exemplary conductance values to aid in navigation of the device through the arterial vasculature of the patient;
identifying the location of the device within the arterial vasculature by comparing the plurality of conductance measurements to an exemplary conductance curve or chart to identify a specific location of the device in the arterial vasculature; and
performing at least one medical procedure at a targeted location within the arterial vasculature, the targeted location navigated to and identified from at least one of the plurality of conductance measurements.

18. A method, comprising the steps of:
inserting at least part of an impedance device into a femoral artery of a patient, the at least part of the impedance device comprising a solitary electrode;
generating an electric field from the solitary electrode on the at least part of the impedance device within a patient's body;
obtaining a first conductance measurement from the solitary electrode while a distal end of the impedance device is positioned within an arterial vasculature of the patient at a first location, the first location being the femoral artery;
obtaining a second conductance measurement from the solitary electrode, the second conductance measurement comprising an increase from the first conductance measurement, while the distal end of the impedance device is positioned within the arterial vasculature at a second location, the second location being an iliac artery;
moving the distal end of the impedance device to a third location within the arterial vasculature based upon a comparison of the first conductance measurement and the second conductance measurement to a first prior conductance measurement for the first location and a second prior conductance measurement for the second location, respectively;
moving the distal end of the impedance device to a fourth location within the arterial vasculature based upon at least the third conductance measurement; and
ultimately moving the distal end to a final location, said movement performed based upon the comparison of conductance measurements obtained within the arterial vasculature to prior conductance measurements;
wherein the preceding steps of moving the distal end of the impedance device to the second, third and fourth location are done without using x-ray or other imaging devices;
performing at least one medical procedure at a target location within the arterial vasculature; and wherein the at least one conductance measurement of the first conductance measurement, the second conductance measurement, the third conductance measurement, and the fourth conductance measurement includes at least one characteristic indicative of the corresponding first, second, third, and fourth location within the arterial vasculature.

19. The method of claim 18, wherein the first conductance measurement, the second conductance measurement, the third conductance measurement, the fourth conductance measurement, and the one or more additional conductance measurements are each obtained using a detector of the impedance device.

20. The method of claim 1, further comprising the step of identifying a location of the device within the arterial vasculature by comparing the at least one characteristic to an exemplary conductance curve or chart.

\* \* \* \* \*